United States Patent [19]
Zhu et al.

[11] Patent Number: 5,301,658
[45] Date of Patent: Apr. 12, 1994

[54] MEMBRANE ENDOSCOPIC RETRACTOR

[75] Inventors: Yong Hua Zhu, Loma Linda; Wolff M. Kirsch, Redlands, both of Calif.

[73] Assignee: Loma Linda University Medical Center, Loma Linda, Calif.

[21] Appl. No.: 874,536

[22] Filed: Apr. 27, 1992

[51] Int. Cl.$^5$ .......................................... A61B 17/02
[52] U.S. Cl. ..................................... 128/20; 606/191
[58] Field of Search ...................... 128/20, 3, 17, 18; 600/37; 606/121, 191, 198, 205, 215, 60; 604/104, 105, 106, 107, 108, 109; 273/29 B, 29 BA; 116/173; D11/165, 166

[56] References Cited

U.S. PATENT DOCUMENTS

| | | |
|---|---|---|
| 401,082 | 4/1889 | Taylor .................. 273/29 BA |
| 1,275,520 | 8/1918 | Bell ........................ 128/20 |
| 3,299,883 | 1/1967 | Rubens . |
| 3,570,475 | 3/1971 | Weinstein . |
| 4,190,042 | 2/1980 | Sinnreich . |
| 4,573,452 | 3/1986 | Greenberg ............. 128/20 |
| 4,611,594 | 9/1986 | Grayhack et al. . |
| 4,760,849 | 8/1988 | Kropf ................... 606/191 |
| 4,813,401 | 3/1989 | Grieshaber ............ 128/17 X |
| 4,889,107 | 12/1989 | Kaufman ............... 128/20 |
| 4,921,484 | 5/1990 | Hillstead .............. 604/104 |
| 4,993,719 | 2/1991 | Hernandez ............ 273/29 B |
| 4,994,070 | 2/1991 | Waters . |
| 5,006,106 | 4/1991 | Angelchik . |
| 5,024,551 | 6/1991 | Hinterholzer ......... 116/173 X |
| 5,112,310 | 5/1992 | Grobe ................... 604/105 X |
| 5,178,133 | 1/1993 | Pena ...................... 606/198 X |
| 5,183,033 | 2/1993 | Wilk ..................... 606/191 X |

FOREIGN PATENT DOCUMENTS

| | | |
|---|---|---|
| 0246086 | 5/1983 | European Pat. Off. . |
| WO83/03189 | 9/1983 | PCT Int'l Appl. . |
| 2193141 | 2/1988 | United Kingdom ............. 606/205 |

OTHER PUBLICATIONS

Kuzmak, "Silicone Gastric Binding", *Contemporary Surgery*, Jun. 1986, p. 14.

Primary Examiner—Richard J. Apley
Assistant Examiner—Karen A. Jalbert
Attorney, Agent, or Firm—Knobbe Martens Olson & Bear

[57] ABSTRACT

A membrane endoscopic retractor is disclosed for retracting organs and tissue inside the body using only small tools extending through short incisions in the body. The membrane retractor generally comprises a membrane for supporting tissue and organs and two or more probes for supporting the membrane. The probes are endoscopic devices which allow the user to place and manipulate the membrane inside a body by stretching and supporting the membrane between and along various points. The membrane is rollably arranged inside a housing on one probe so as to easily be inserted into the body and then extended therefrom by a second probe. A third probe may be used to provide additional support to the membrane between the first and second probes. The entire retraction procedure inside the body is manipulatable from control ends of the probes which are located outside of the body.

34 Claims, 6 Drawing Sheets

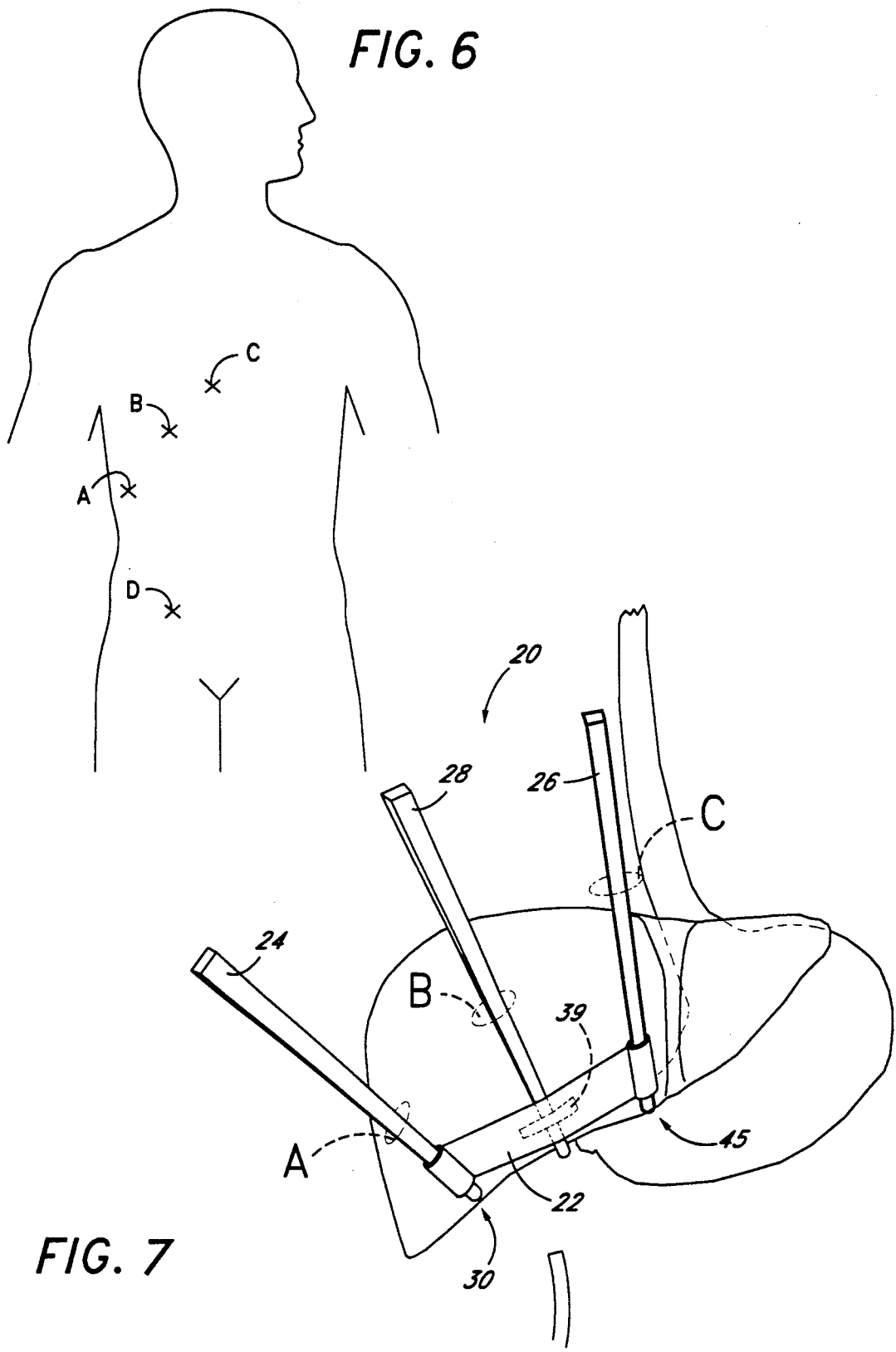

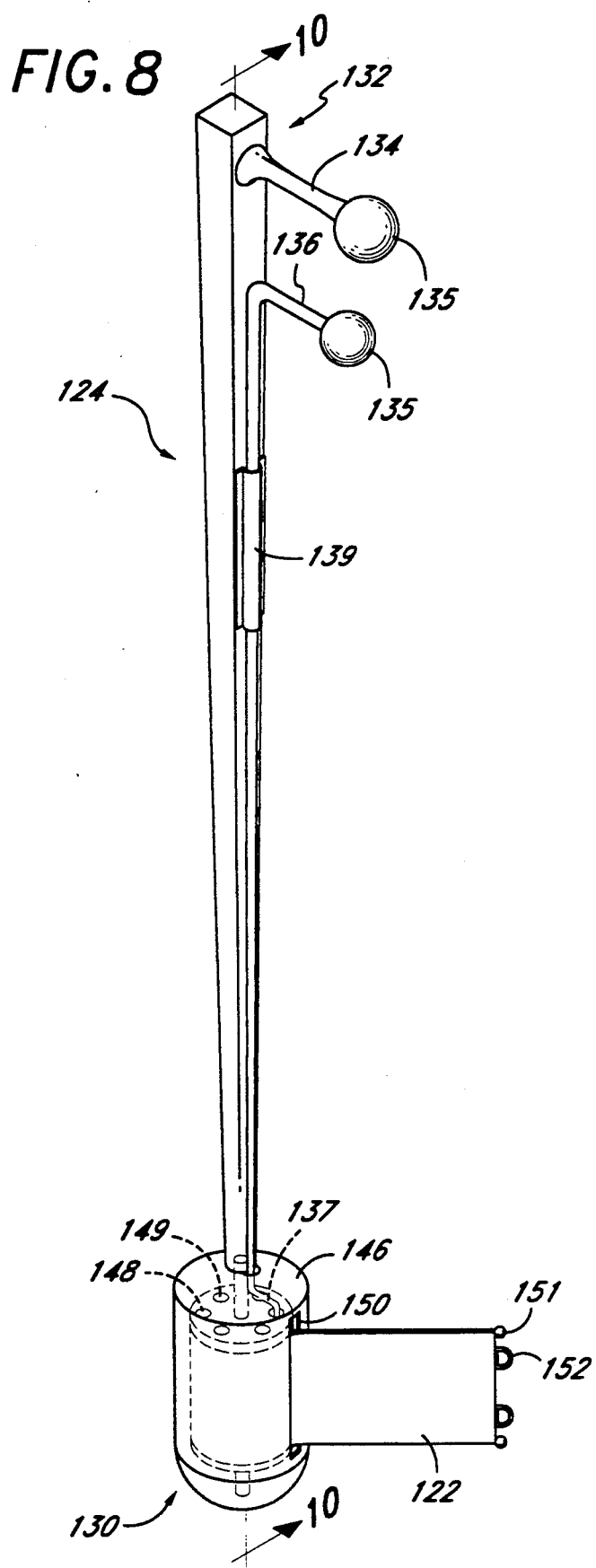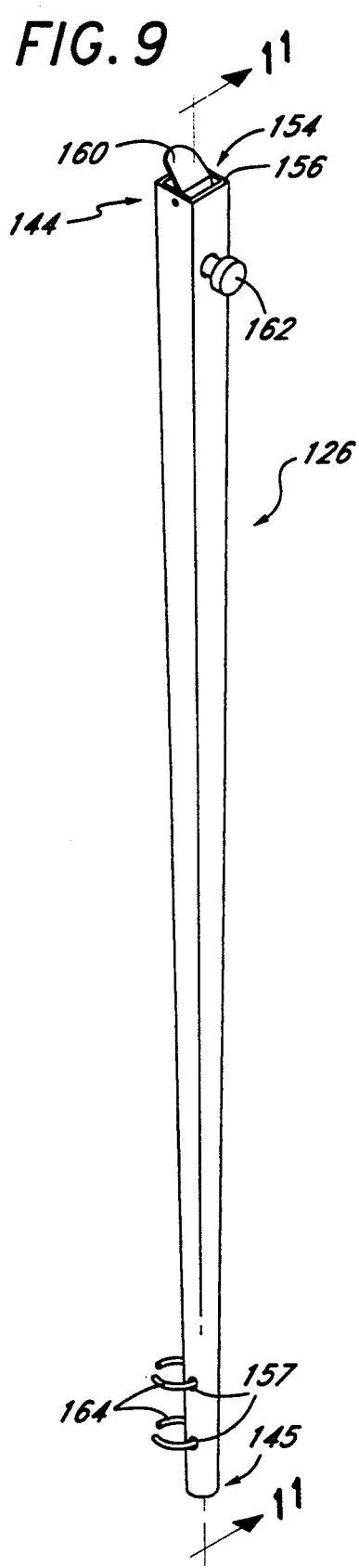

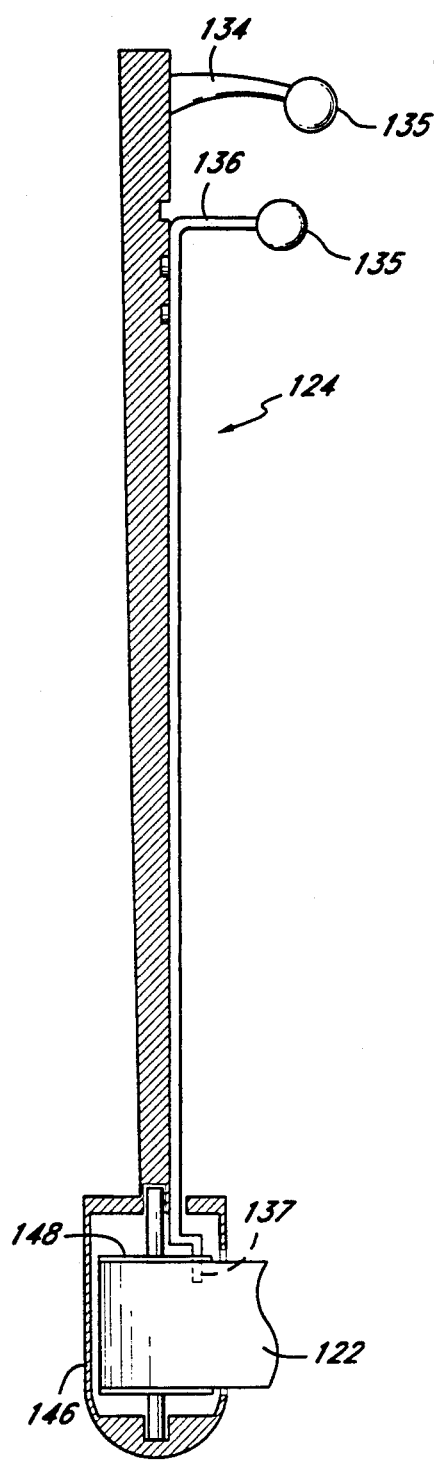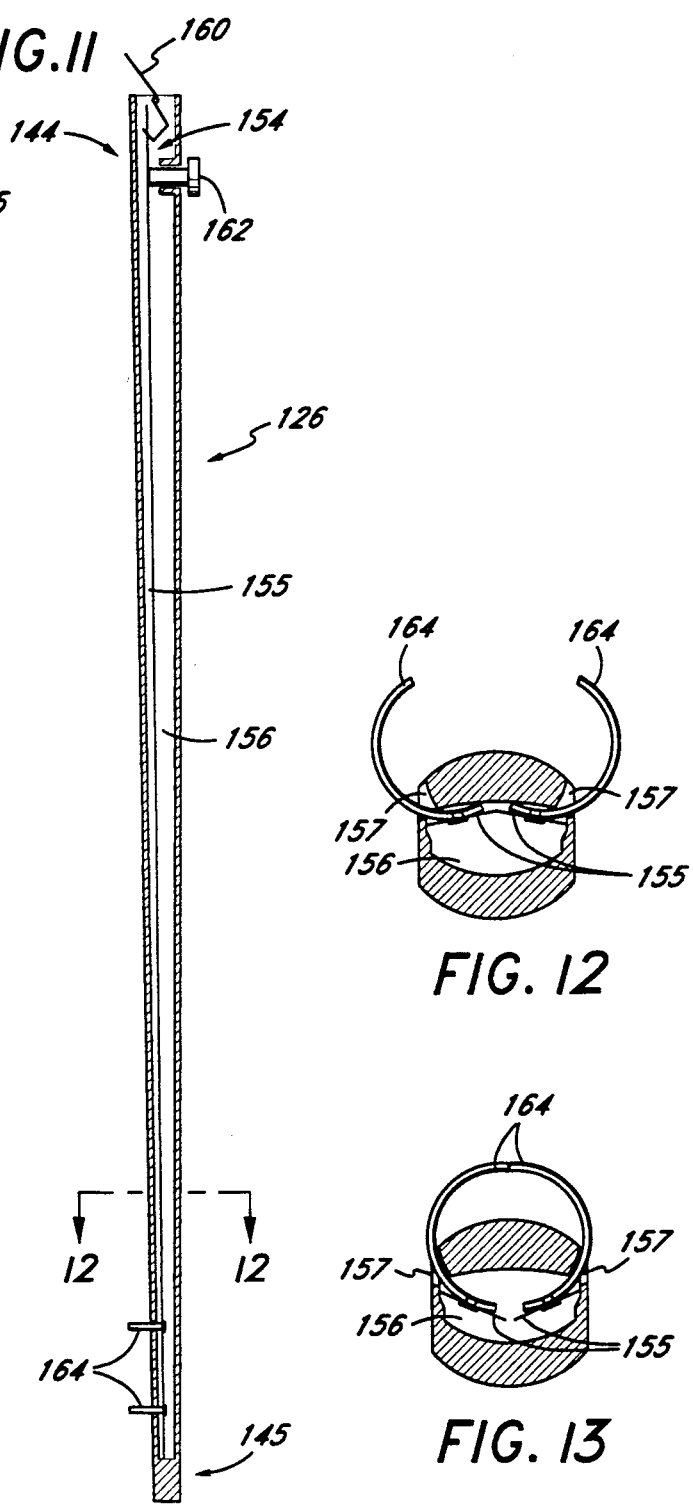

MEMBRANE ENDOSCOPIC RETRACTOR

FIELD OF THE INVENTION

The present invention relates to retractors used in surgery. More specifically, the invention relates to a retractor having a membrane stretchable between various probes by which an internal organ or other internal body part may be retracted during endoscopic surgery.

BACKGROUND OF THE INVENTION

The field of endoscopic surgery has been advancing rapidly in recent years. In this form of surgery, procedures are performed inside of the body of a patient using instruments inserted through small endosurgical ports. The surgery is performed with the aid of an endoscope, which is a thin, tube like instrument featuring a light source, viewing lenses, and/or various other attachments such as irrigators, scissors, snares, brushes, or forceps. Endoscopes may be flexible or rigid, and normally utilize optic fibers to transmit light to the internal cavity. The surgery is normally viewed by the surgeon through an ocular. Lenses are placed near the tip of the endoscope and the image thereon is transmitted via optic fibers or other lens systems, to the ocular or viewer. Other types of endoscopes utilize optical fibers to transmit electronic signals representing the internal image from the distal lens to a video monitor which is viewed by the surgeon.

This form of surgery allows internal visualization of the body structure without the necessity of excessive dissection of tissue. Typical endoscopes often are in the 5 to 12 mm diameter range and thus require only very small incisions for insertion into the body.

This form of surgery has developed rapidly because of the numerous benefits arising in favor of the patient. Since there is only a small incision to permit entrance of the endoscope, endoscopic surgery results in less trauma to the patient's body and faster patient recovery. For the benefits of endoscopic surgery to arise, however, all aspects of the surgery, such as the initial examination, retraction, and the surgical procedure itself, must be capable of being accomplished through small endoscopic incisions or ports.

The obvious difficulty associated with endoscopic surgery is inadequate visualization of the internal structure required to properly complete the surgical procedure. Endoscopic surgery is thus difficult in areas which are typically difficult to reach, such as the gallbladder. In gallbladder surgery, (or "cholecystectomy") the tissue and organs surrounding the gallbladder are examined with the endoscope and retracted in order to properly expose the organ which is to be removed.

Currently, endoscopic procedures in the abdominal cavity, otherwise known as laparoscopy, often require retraction. Specifically, endoscopic procedures involving the gallbladder entail retracting the liver, which rests directly above the gallbladder. In an open surgery operation, retraction such as this is relatively easy, as the surgery involves the exposure of the entire organ area. In order to obtain the benefits of endoscopic surgery, however, a form of retraction which can be accomplished through endoscopic ports is necessary.

In an endoscopic procedure involving the gallbladder or other abdominal organ, retraction is currently accomplished by inflating the peritoneal cavity with carbon dioxide. This method of retraction requires a small endoscopic port for the introduction of a gas source. The gas is introduced into the body through a trocar, and a state of pneumoperitoneum occurs. The gas inflates the peritoneal cavity so as to cause the skin and muscles to separate and rise above various organs and tissue, creating the exposure necessary to accomplish the endoscopic surgery.

Several problems are associated with pneumoperitoneal retraction, however. First of all, exposure remains adequate only while the required pneumoperitoneal state remains. Since endoscopic surgery normally requires the introduction of at least the endoscope, and more often several other tools, several endoscopic ports will most likely be created in the body. Each of these ports, which normally use a cannula to keep them open for access, in effect create an exhaust port for the gas. The risk that insufflation pressure may be lost increases the risk that the endoscopic procedure may go awry as adequate exposure for the endoscope is extinguished.

Further, there are many complications which are associated with persistent pneumoperitoneum during an endoscopic procedure. Acute cardiovascular collapse secondary to over-distension of the abdomen, vasovagal reflex activation, cardiac arrhythmia, pneumothorax, subcutaneous emphysema, alteration of large vein venous return, retinal hemorrhage, blindness, carbon dioxide embolism, and general patient discomfort have all been associated with persistent pneumoperitoneum.

Lastly, pneumoperitoneal retraction is effective in retracting only the muscles and tissue from above the organs. The organs themselves are not, to a great extent, retracted from each other.

There is therefore a need for a device and method which provides retraction in conjunction with endoscopic procedures which is effective in providing adequate visualization and which is safe and has fewer side effects than current methods.

SUMMARY OF THE INVENTION

In accordance with one aspect of the present invention, there is provided a membrane endoscopic retraction system. The invention permits safe and effective retraction of internal organs and tissue in endoscopic surgery.

Retraction is accomplished with the present invention through the use of a supporting retraction membrane manipulated by endoscopic probes. The membrane is soft and flexible in order to avoid damage to internal organs and tissues; however, it is sufficiently inelastic and rigid so as to provide efficient retraction when placed in tension. The membrane is connected to and coiled inside the insertion end of a first probe. The membrane can be uncoiled from inside the probe once it is inside the body and attached at its free end to a second probe. The membrane can then be tightened between the first and second probes so as to act as a sling which can be used to support various internal organs and tissue. A third probe may be connected to the membrane at a point between the first and second probes if additional support is necessary.

Advantageously, the first probe comprises a rigid manipulatable rod. The insertion end of the first probe is provided with a roller confined within a housing and mounted thereon. The first probe also has a control end which has two handles extending from it. These handles are used both to grip and manipulate the first probe, as well as lock the roller into a desired position.

The membrane is a flexible member which supports the organs and/or tissue to be retracted. As stated above, the membrane is itself supported and manipulated by at least two, and often three, endoscopic probes. One end of the membrane is securely attached to the roller in the housing of the first probe. When being inserted into or retracted from the body, the membrane is normally coiled on the roller located inside the housing on the insertion end of the first probe. One handle of the first probe is normally locked into the roller on which the membrane is coiled during these procedures to keep the membrane stationary. Once manipulated into the body, the lock is released to allow the membrane to be uncoiled so as to be stretched under or around the organ(s) to be retracted.

The free end of the membrane is provided with rings which may be connected to rings correspondingly mounted on the second probe. The rings on the second probe may be opened or closed by external manual manipulation. The free end of the membrane extends from the housing through a slot therein. The membrane is prevented from recoiling into the housing by small beads mounted on the free end edges of the membrane.

The second probe, like the first, is a rigid shaft for endoscopic use. This probe provides the necessary support to sling the membrane under organs to retract them. The second probe has controls located at a control end which can be used to open and close the rings located on the insertion end of the probe corresponding to those on the membrane. In this manner, the rings on the membrane may be securely locked to the rings on the second probe.

The membrane has a small loop on it midway along its length. This loop facilitates the introduction of a third probe. The third probe is a rigid endoscopic shaft which optionally may be used to further support the membrane at a point between the first and second probes. This is advantageous when, for example, a large organ such as the liver, is to be retracted. The third probe supports the membrane by engaging the small loop of material thereon.

All of the probes may be hollow tubular devices to allow the introduction of various devices, such as other retractors, a device for suction, or an endoscope. Further, one of the probes may have a hollow passageway to allow the introduction of a unipolar cauterizer. The probe in this instance acts as an insulator for the bovie instrument.

The endoscopic membrane retractor of the present invention does not have the dangers associated with continuous pneumoperitoneal retraction. The present invention can be placed with only initial insufflation to provide easy insertion of the device. After insertion, retraction can be maintained simply and safely with the membrane.

The membrane retractor is advantageously quite small, which allows its introduction into the body through cannulas placed in small trocar openings. The membrane retractor is normally introduced through two, or if the third probe is used, three, of these small openings.

The membrane retractor is much more effective in retracting organs, especially larger ones, than insufflation. The invention allows the surgeon or assistant to manually retract an organ to any extent necessary, merely by manipulating one or more of the probes. The probes are easily manipulatable into any variety of angles and positions to provide exact retraction at any location. This is in contrast to the insufflation method, where the gas indiscriminately fills the body cavity.

Further, this retractor is adaptable for use on organs of various sizes. By merely adjusting the length of the membrane which is uncoiled, the membrane retractor can be sized to fit nearly any organ.

BRIEF DESCRIPTION OF THE DRAWINGS

FIG. 6 is a diagram showing the entry points of the probes and an endoscope in gallbladder endoscopic surgery.

FIG. 7 is a perspective view of the abdomen of a patient illustrating how the endoscopic membrane retractor retracts the liver for gallbladder surgery.

FIG. 8 is a perspective view of an alternate embodiment of the first probe.

FIG. 9 is a perspective view of an alternate embodiment of the second probe.

FIG. 10 is a cut-away side view of the first probe in FIG. 8 taken along line 10—10 of FIG. 8.

FIG. 11 is a cut-away side view of the second probe of FIG. 9 taken along line 11—11 of FIG. 9.

FIG. 12 is a cut-away view of the second probe of FIG. 11 taken along line 12—12 of FIG. 11 with the rings in the open position.

FIG. 13 is a cut-away view of the second probe of FIG. 11 taken along line 12—12 of FIG. 11 with the rings in the closed position.

DETAILED DESCRIPTION OF THE INVENTION

Figure 1:
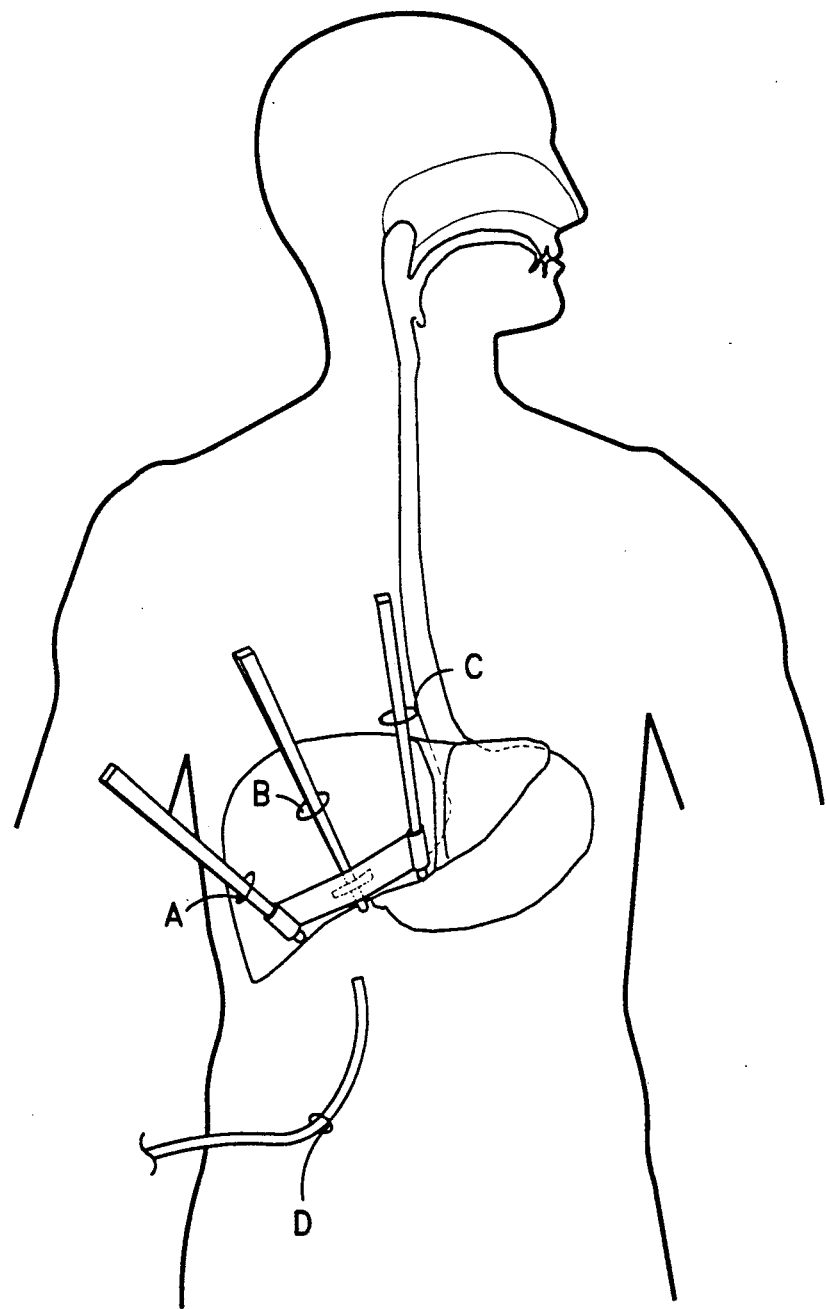
FIG. 1 is a schematic view of a patient illustrating the general manner in which the membrane retractor of the present invention may be utilized during endoscopic surgery.

Referring to FIG. 1, there is shown a schematic view of a patient illustrating only one example in which the membrane retractor of the present invention might be utilized during endoscopic surgery. In particular, the various probes of the present invention are inserted through small surgical openings or ports made in the body to receive such probes or other instruments such as an endoscope, etc. The membrane of the present retractor, mounted along the insertion ends of the various probes is utilized to constrain and retract various tissues and organs to permit endoscopic surgery. In addition, an endoscope may be inserted in yet another port, as shown in FIG. 1, in order to permit visualization of the surgical region. It should be noted, however, that the principles of the present invention are not limited to the probe placement or type of surgery illustrated in these drawing figures, which are exemplary in nature.

Figure 2:
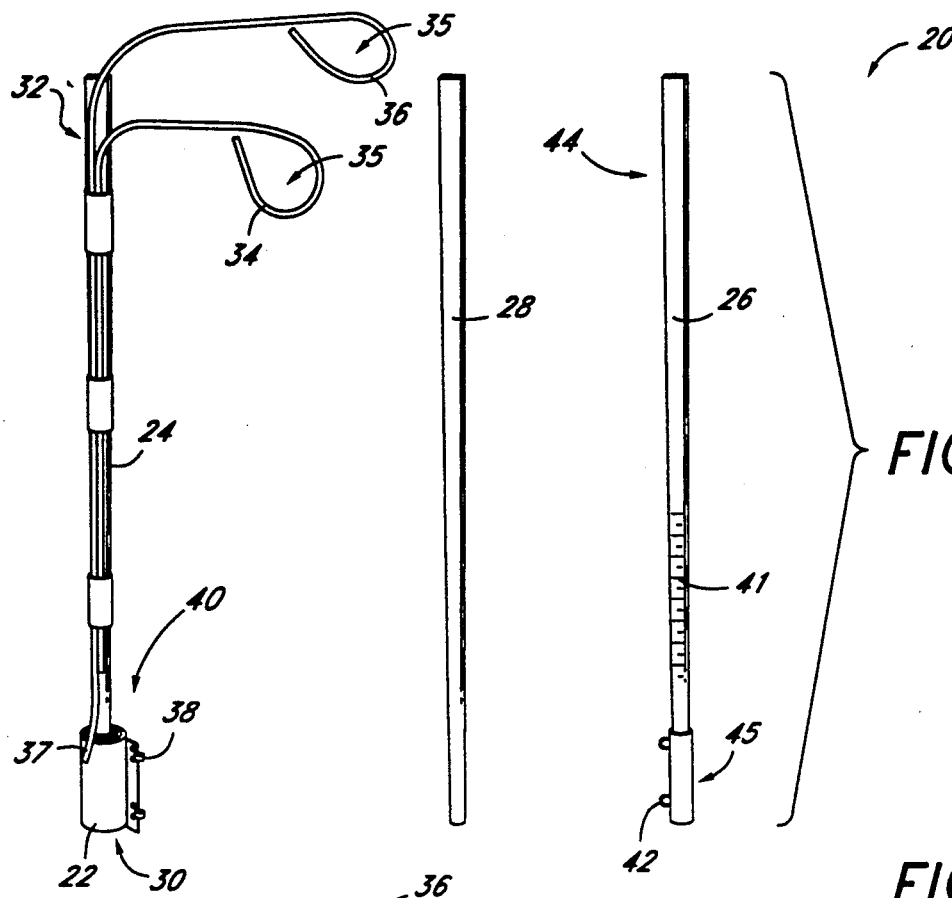
FIG. 2 is a perspective view of a first embodiment of the membrane endoscopic retractor of the present invention.

Referring to FIG. 2, there is shown in more detail the membrane endoscopic retractor 20 of the present invention. FIG. 1 shows a membrane 22, and a first probe 24, a second probe 26, and a third probe 28 which are used to position the membrane during surgery.

The first probe 24 is a rigid shaft. The probe 24 may be of any desired length, depending primarily on the particular intended application. The probe 24 illustrated is typically used for gallbladder removal, and is approximately 12 inches long; although, of course, other suitable lengths are contemplated.

As illustrated, the probe 24 has a cross section which is circular at an insertion or distal end 30, and a cross section which is rectangular at a control or proximal end 32. The insertion 30 and control end 32 diameters, like the length, are a function of the intended use. For gallbladder removal, the above dimensions have been chosen to optimize strength and rigidity in the probe 24, and yet minimize the probe volume which is introduced into the body cavity.

The probe 24 is preferably made of a material which is free from degradation and which is sterilizable and biocompatible. Stainless steel works well. The probe 24 can also be made of some other material, such as regular steel, and then coated with an outer sheath which has the desired material qualities.

The probe 24 is blunt on its insertion end 30, the tip preferably being somewhat rounded. The shape of the insertion end 30 is chosen to aid in preventing the puncture or slicing of internal organs and tissue when the probe 24 is being manipulated inside the patient's body. The control end 32 of the probe 24 is, as discussed above, of a square cross section. The control end 32 may be shaped in any manner; however, the shape is preferably designed to aid in easy gripping with a hand and/or placement in a secondary stationary holder (not shown).

Advantageously, the first probe 24 has a series of marks (not shown) placed on its outer surface. These marks begin a short distance from the membrane 22 and extend up the probe 24 towards its control end 32. The marks preferably represent length gradations. The marks are used to aid in the placement of the retractor 20 by providing a measurement of the depth at which the probe 24 is extended into the patient's body.

Still referring to FIG. 2, a first handle 34 and second handle 36 extend from the first probe 24 on the control end 32. The handles 34, 36 like the probe 24, are preferably manufactured from a material which is free from degradation and is sterilizable and biocompatible, such as stainless steel. The first handle 34 is a short member extending nearly perpendicular to the axis of the probe 24 a distance of about 3 inches. The second handle 36 is an elongated member which is partly located parallel to the probe 24 and then extends perpendicular to the probe 24 in the same plane as the first handle 34 at a point proximal to the first handle 34. The second handle 36 extends out from the probe 24 at this point about 4 inches. The handles 34, 36 have small loops 35 at their proximal ends for acceptance of a finger.

The first handle 34 is attached to the first probe 24 with small screws (not shown), although it could be formed as part of the probe 24 itself or welded or brazed thereon. The elongated portion of the second handle 36 has a tip 37 which is angled on its surface which faces the probe 24. The second handle 36 is slidably affixed to the probe 24 with pins (not shown) which extend into slots (not shown) in the probe 24. This allows the second handle 36 to move along the slots in the probe 24 so that the tip 37 of the second handle 36 may be moved into a locked position where the tip 37 extends over the membrane 22 to keep it from unrolling, and an unlocked position where the tip 37 does not extend over the membrane 22 and the membrane may be rolled or unrolled.

Figure 3:
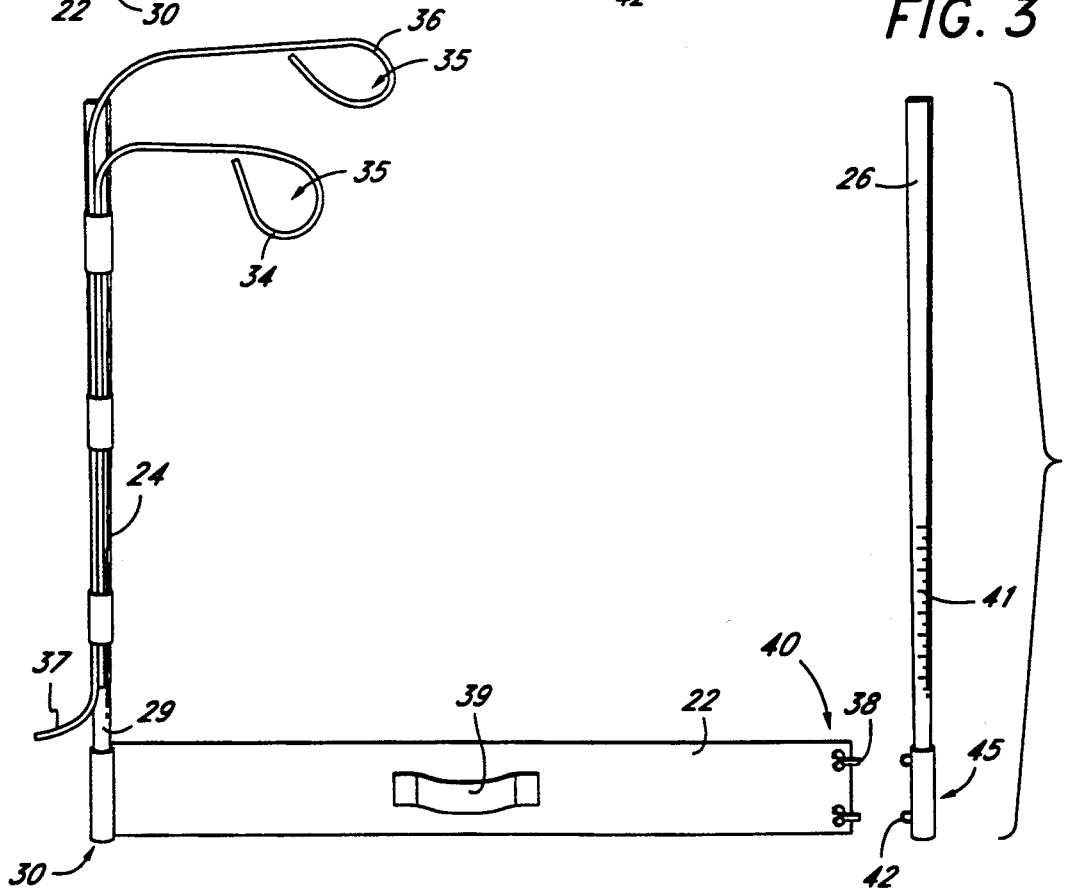
FIG. 3 is a perspective view of the first and second probes in FIG. 1 with the membrane extended.

Referring to FIG. 3, the membrane 22 is located on the insertion end 30 of the first probe 24. The membrane 22 is affixed securely at one end to the insertion end 30 of the first probe 24. The membrane 22 may be affixed by gluing or other attachment means well known in the art. The membrane 22 is a flexible, soft, and somewhat elastic member. The membrane 22 material is preferably also a material which does not absorb liquid, and which is sterilizable. As illustrated, the membrane 22 is made of rubber or other polymeric material.

As illustrated in FIGS. 2 and 3, two hooks 38 are affixed to a free end 40 of the membrane 22. The hooks 38, as shown, are curved metal pieces which are attached to the membrane 22 and curve outwardly away from the surface of the membrane. The hooks 38 are chosen to be easily retrieved by corresponding rings 42 on the second probe 26, which will be described in more detail below. The hooks 38 are of a low profile so as to not interfere with the manipulation of the first probe 24. The hooks 38, like the first probe 24, are preferably manufactured from a material which is free from degradation and contamination. It is contemplated that other attachment means may be used which are well known in the art.

A small loop 39 is mounted at a point nearly half way along the length of the membrane 22. This loop 39 is made of the same material as the membrane 22. The loop 39, as illustrated, is formed by attaching a small strip of the membrane material at each of its ends, to the membrane 22 itself. This may be done by gluing, sewing, or other attachment means. This loop 39 forms a point of engagement for the third probe 28, which will be described later.

The second probe 26 is much like the first probe 24, except that the second probe does not have handles or the membrane attached directly to it. The second probe 26, like the first probe 24, is a rigid shaft member. The second probe 26 is normally of the same length as the first probe 24, although other lengths are contemplated. The length is primarily determined by the type of operation in which the retraction is engaged. The second probe 26 preferably also has marks 41 on its outer surface for measuring the depth of penetration, much like the first probe 24.

As illustrated in FIGS. 2 and 3, the shape of the second probe 26 is the same as the first probe 24. It is contemplated, however, that the second probe 26 may have control end 44 which is somewhat different in shape than that of the first probe 24 if, for example, the second probe is to be positioned in secondary stationary tool holder during use.

Figure 4:
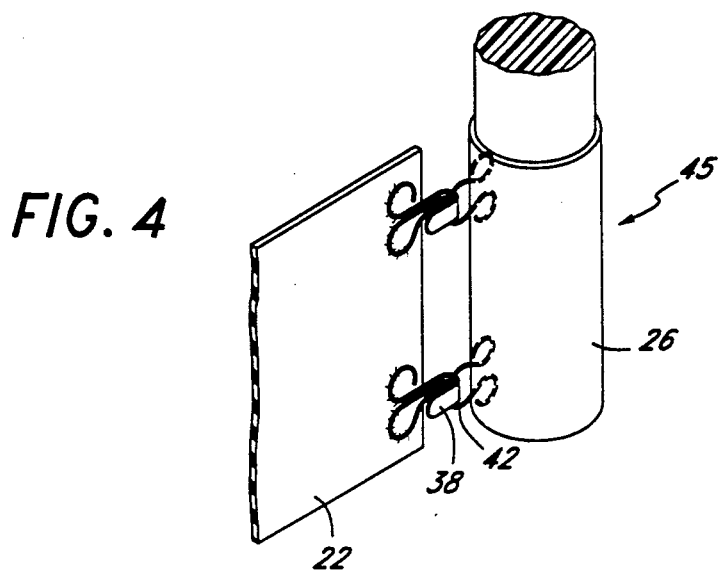
FIG. 4 is an enlarged perspective view of the hook and ring connection between the membrane and second probe of the first embodiment.

FIG. 4 illustrates the manner in which the hooks 38 of the membrane 22 interconnect with the rings 42 on the second probe 26. Rings 42 are mounted on an insertion end 45 of the second probe 26. These rings 42 correspond to the hooks 38 mounted on the membrane 22. The rings 42, as illustrated, are small metal pieces which are brazed to the insertion end 45 of the second probe 26. Other attachment means such as welding, gluing or other means well known in the art are contemplated. The rings 42 may also be molded or cast as part of the probe 26.

The third probe 28 is nearly identical to the second probe 26. The third probe 28 shown in FIG. 2 is merely a rigid shaft having lengths and diameters similar to those described for the first probe 24 and second probe 26. The third probe 28 is likewise made of stainless steel or other material which is free from degradation and which is sterilizable and biocompatible. Like the first and second probes 24, 26, the third probe 28 preferably also has the marks (not shown) on its outer surface for measuring the depth of penetration.

Figure 5:
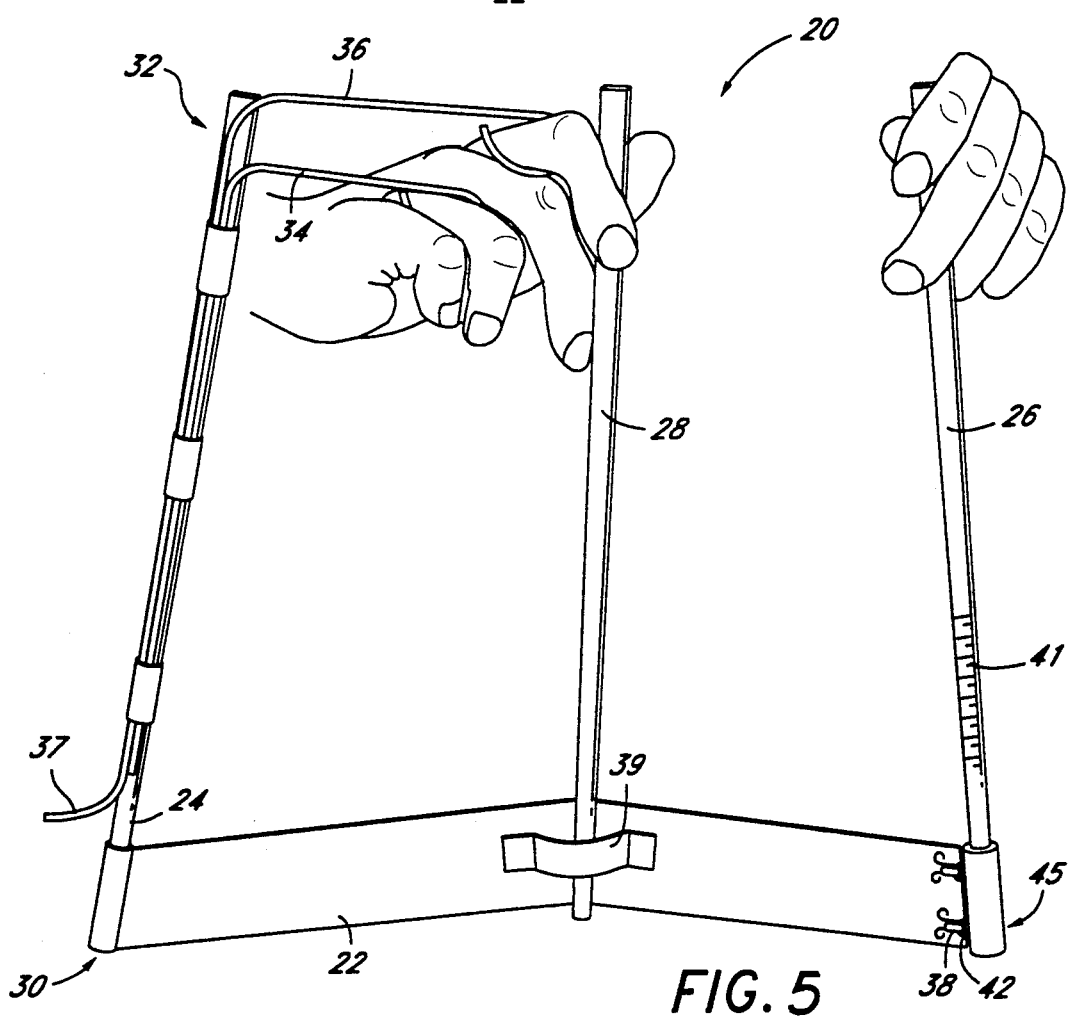
FIG. 5 is a perspective view illustrating a manner in which all three probes of FIG. 1 may be used to support the membrane.

Referring to FIG. 5, the manner in which the retractor 20 of the present invention may be manually manipulated is illustrated. In one use of the present invention, the first probe 24 with the membrane 22 rolled up on its insertion end 30 and retained in place thereof by the tip 37 is inserted into a surgical port as explained below in more detail. The second probe 26 is then inserted into the patient's body through the second port and manipulated so that the hook 38/ring 42 connection illustrated in FIG. 4 may be implemented. This connection permits the second probe 26 to unroll the membrane 22 from the first probe 24, as shown in FIG. 5. Likewise, the second probe 26 can extend the membrane 22 to its fullest extent or may shorten the length of the membrane 22 by wrapping the membrane around its insertion end 45 (not shown).

Upon insertion of the first probe 24, as explained above, the rolled membrane 22 is retained in position by means of the tip 37. Once inserted to the desired distance, the membrane 22 can be unlocked by manipulating the second handle 36. Once the membrane 22 is extended to the desired length, the first 24 and second 26 probes can be manually manipulated by the hands of the surgeon. In addition, the extending handles 34,36 of the first probe 24 permit the surgeon to simultaneously hold the first probe 24 and the third probe 28, as illustrated in FIG. 5. This permits the increased tension and manipulation on the membrane for additional retraction functionality. It should be noted that endoscopic surgery of the type illustrated here often requires more than one surgeon. For example, one surgeon or other assistant may be necessary to manipulate the retraction device, such as that illustrated in the present invention, while another surgeon completes the desired surgical procedure. Furthermore, the present invention is capable of various manual manipulations and should not be considered limited to those illustrated in the drawing figures.

As can best be seen in FIG. 5, all three probes 24, 26, 28 may be held in place by one assistant. This may be accomplished by holding the first probe 24 by placing a finger through each of the handles 34, 36. The third probe 28 is then held by the same hand which is holding the first probe 24 by directing the handles 34, 36 towards the third probe 28. As can now be seen, the length of the handles 34, 36 are chosen for this particular application so that when the first probe 24 and third probe 28 are at their respective locations in the patient's body, the handles 34,36 are of sufficient length so that the first 24 and third 28 probes may both be grabbed at the same time. The position of the second probe 26 is easily maintained with the other hand.

All three probes 24, 26, 28 may, of course, be held in any other manner which is comfortable for the user. It is also contemplated that a secondary frame (not shown) which is rigid and maneuverable, could be used to station the probes.

Referring to FIGS. 5-7, the operation of the membrane endoscopic retractor 20 will now be explained as used in a cholecystectomy procedure.

The body is first prepared by introducing a state of pneumoperitoneum to aid in the placement of the membrane endoscopic retractor 20. As illustrated in FIGS. 6 and 7, the insertion end 30 of the first probe 24, with the membrane 22 withdrawn or recoiled, is inserted into the patient's body though a cannula which is inserted into trocar opening A. An endoscope, which is inserted at point D into the body, is used to view and direct the proper placement of the first probe 24 under the right anterior segment of the liver.

With the first probe 24 in place, the insertion end 45 of the second probe 26 is inserted through a cannula inserted into trocar opening C. The second probe 26 thus enters the body a distance away from the first probe 24. As explained above, the second probe 26 is then manipulated towards the first probe 24. The second probe 26 is manipulated such that the rings 42 are securely connected to the hooks 38 fastened to the membrane 22. It is contemplated that other attachment means, well known to those skilled in the art, may be used to connect the second probe 26 to the membrane 22. The second probe 26 is then guided away from the first probe 24 towards its final location under the left medial segment of the liver. As the second probe 26 is moved away, the membrane 22 is uncoiled from the first probe 24. The uncoiling of the membrane 22 is accomplished by moving the second handle 36 of the first probe 24 into its unlocked position. The first probe 24 is then rotated while the second probe 26 is maneuvered away from the first probe 24, so that the membrane 22 is uncoiled.

Once the second probe 26 is in its final position, the second handle 36 securing the membrane 22 is returned to its locked position to prevent the membrane from further unravelling from the first probe 24. The third probe 28 is then, if needed, inserted into the peritoneal cavity. The third probe 28 may be inserted into the cannula in which the first probe 24 or second probe 26 is located, or as illustrated, be inserted into the body through a cannula inserted into trocar opening B.

The third probe 28 is guided into the body and slid securely into the loop 39 on the membrane 22. The three probes 24, 26, 28 are then manipulated so as to raise the right lobe of the liver so as to slightly expose the gallbladder. At this time, the retraction, as necessary for procedures involving the gallbladder, will be sufficient, and the condition of pneumoperitoneum may be allowed to lapse. The gallbladder treatment may then be successfully completed.

Once the procedure has been completed, the probes 24, 26, 28 must be removed. This is accomplished by first removing the third probe 28 from the body. The second probe 26 is then disconnected from the membrane 22 and removed. The membrane 22 is then coiled back upon the insertion end 30 of the first probe 24 and locked into place. The first probe 24 is then removed from the body.

Referring to FIGS. 8-13, there is shown an alternate preferred embodiment of the present invention. This retractor also comprises three probes 124, 126, 128 not shown and a membrane 122.

The first probe 124 is much like that described above, being a shaft having an insertion end 130 and control end 132, except that it has a housing 146 mounted thereon at its insertion end 130. The housing 146 is a hollow cylinder welded onto the shaft of the probe 124. The housing 146 contains a spring biased roller 148 which may rotate in the housing. The membrane 122 is affixed at one end to the roller 148. The other end of the membrane 122 extends from the roller 148 through a slot 150 in the housing 146. The slot 150 is an opening in the housing 146 slightly wider than the membrane 122 and slightly taller. In this fashion, the membrane 122 can be coiled inside the housing 146, or may be uncoiled and extended therefrom through the slot 150. The housing 146 may optionally have a distal end which is removable, so that the roller 148 and membrane 122 located thereon can be taken out of the housing for sterilization or replacement. Mounting the membrane 122 in the housing 146 protects the membrane, as well as allows the membrane 122 to be coiled and uncoiled easily inside the body since no tissue may get against the membrane 122 to cause resistance. The dimensions of the rest of the probe 124, as well as its material, are primarily as described above.

The first handle 134 is primarily the same as the first handle 34 described above except that instead of finger loops at its end, this handle 134 has a small gripping sphere 135, which is easily gripped between two fingers or inserted into a probe holder (not shown). The second handle 136 has the same type of gripping sphere 135, except smaller than that on the first handle 134. The second handle 136 extends out from the probe 124 and then down along the probe 124 as before, except that its tip 137 extends into the housing 146. The roller 148 has holes 149 in its end into which the tip 137 of the second handle 136 may be extended. In this fashion, the second handle 136 may be extended into a hole 149 in the roller 148, as shown in FIG. 8, so as to prevent the roller 148 from rotating. The second handle 136 also has an unlocked position where the tip 137 is retracted from one of the holes 149 in the roller 148 so as to allow the roller 148 to rotate and the membrane 122 to be coiled or uncoiled. The second handle 136 is slidably engageable into either of these two positions by having a collar 139 (FIG. 8) mounted over it near the control end 132 of the probe 124, which frictionally engages the handle 136.

The membrane 122 is as described above, having the same length and width, and being of the same material. The membrane 122 also has a loop (not shown) mounted in its middle as before to allow the introduction of the third probe 128. As shown in FIG. 8, instead of hooks being mounted on the membrane 122, this membrane 122 has rings 152 mounted thereon. The rings 152 are loops sized to allow the introduction of rings 164 on the second probe 126, as will be described below, and are preferably made of stainless steel and mounted parallel to the plane of the membrane 122. Small beads 151 are mounted on the outer edges of the membrane 122 at its free end. The beads 151 are slightly larger in diameter than the slot 150 in the housing 146 is wide so as to prevent the membrane 122 from being coiled completely within the housing 146.

Referring to FIG. 9, the second probe 126 is primarily as described above in dimension and material, except that the second handle 126 has a control 154 located in a hollow passage 156 which extends from the control end 144 to a point near the insertion end 145 in the probe 126. The control 154 comprises two elongated flat spring members 155 (FIG. 11), a releasing tab 160 and an engaging button 162. The control 154 is similar to that used in a three-ring notebook binder. The spring members 155 are thin, flat and preferably made of steel. The outer edges of the spring members 155 extend against the walls of the passage 156, while the inner edges of the members 155 interlock with tabs (not shown) to prevent them from separating and yet allow them to move with respect to one another.

The members 155 extend inside the passage 156 from near the distal or insertion end 145 to the control end 144 of the second probe 126. The releasing tab 154 is connected to the members 155 and extends out the top of the passage 156. The releasing tab 154 is an L-shaped member, having a portion which is outside the passage 156 at about 45 degrees to the longitudinal axis of the probe 126, and having a second portion which is located inside the passage and which has U-shaped grooves (not shown) into which the members 155 extend.

The engaging button 162 is a short shaft having one end which is sized to accommodate a finger or thumb and which is located outside of the probe 126. The button 162 extends into the probe 126 through a small hole therein, where its other end engages both members 155 where they meet in the center of the passage 156.

As shown in FIGS. 12-13, two sets of partial rings 164 are attached to the members 155 near the distal end 145 of the probe 126. The rings 164 are like those described in the first embodiment, except here they are openable and closable. The rings 164 are located a distance apart corresponding to the distance the rings 152 on the membrane 122 are apart. The partial rings 164 extend from each member 155 inside the probe 126 through curved passageways 157 to the outside of the probe 126. The curved passage ways 157 are sized to allow the rings 164 to move into open or closed positions. The length of the partial rings 164 are chosen so that when the partial rings 164 are in their closed position they engage one another, forming a closed loop. The length of the partial rings 164 is also chosen so that when the engaging button 162 is actuated, the partial rings 164 open so as to leave a gap between them sufficient to allow the introduction of the rings 152 on the membrane 122. The control 154 thus allows the user to create a locked loop around the rings 152 on the membrane 122. This prevents the membrane 122 from coming loose from the second probe 126, as might otherwise happen in the first embodiment.

The third probe 128 (not shown) is primarily as described above.

All three probes 124, 126, 128 may have notches (not shown) etched on the outer surface of the probes in order to aid the user in gauging the depth at which the probe being used is inserted.

In operation, the first and second probes 124, 126 are inserted into the body as described above. When inserted, the second handle 136 of the first probe 124 is in its locked position, and the control 154 of the second probe 126 is in a position corresponding to that where the loop is closed.

Once inserted, the second probe 126 is manipulated next to the membrane 122 and the first probe 124. The engaging button 162 is pushed, forcing the partial rings 164 open as the members 155 are pushed inwardly, as illustrated in FIG. 12. When members 155 move inwardly they simultaneously push releasing tab 160 up into a position where it is ready to be depressed. The second probe 126 is then manipulated so that the rings 152 on the membrane 122 fall between the gap in the open rings 164 on the second probe 126. The releasing tab 160 is then pushed downward, closing the partial rings 164 on the second probe 126 and locking the membrane 122 to the second probe. When the releasing tab 160 is depressed, it pushes members 155 outward, causing the partial rings 164 to pivot with them into a closed position, as illustrated in FIG. 13. As the members 155 move outward, they push the engaging button 162 back out into a position where it is ready to be depressed.

The second handle 136 on the first probe 124 is then moved to its unlocked position, and the second probe 126 is moved away from the first probe 124 to uncoil the membrane 122. When the membrane 122 has been uncoiled as far as necessary, the second handle 136 may be moved back into its locked position so that the membrane 122 does not further uncoil, and is not recoiled by the spring biased roller 148.

The third probe 128 (not shown) may the be used, if necessary, as described above to provide additional membrane 122 support.

To remove the retractor, the rings 164 on the second probe 126 are opened, and the membrane 122 is released. The membrane 122 automatically recoils into the housing 146. The probes 124, 126 may then be removed.

In either of the above embodiments, the probes 24, 26, 28, 124, 126, 128 may, of course, be rigid hollow tubes containing various endoscopic devices, the selection of which would be apparent to one skilled in the art. This is advantageous, for it allows the user to view and perform various functions, such as suction and irrigation. Further, one of the probes 24, 26, 28, 124, 126, 128 may contain a hollow passageway for the introduction of a unipolar cauterizer. The probe in this case can act as an insulator, protecting tissue from burns caused by the cauterizer.

It is contemplated that a greater number of probes be used in supporting the membrane. However, three probes have been disclosed in use here, as it is desirable to prevent the number of incisions and trauma to the internal organs and tissue from being excessive.

Although this invention has been described in terms of certain preferred embodiments, other embodiments that are apparent to those of ordinary skill in the art are also within the scope of this invention. Accordingly, the scope of the invention is intended to be defined only by reference to the following claims.

What is claimed is:

1. A retractor adapted for use in endoscopic surgery, comprising:
    a first elongate probe having a distal portion and a proximal portion, said distal portion being adapted to be removably inserted through a small incision in the body of a patient, said proximal portion remaining externally of the body for manipulation by the surgeon;
    an elongate flexible membrane having a fixed edge and a free edge, said fixed edge being permanently mounted on said distal portion of said first probe and adapted to be inserted therewith into said patient through said small incision;
    said membrane being capable of selectively assuming (i) a first position with respect to said first probe in which said membrane is compactly stored on said distal portion of said first probe for insertion into and withdrawal from said body of said patient, and (ii) a second position in which said membrane is at least partially deployed with respect to said distal portion of said first probe whereby retraction may occur; and
    a second elongate probe having a distal portion and a proximal portion, said distal portion being adapted to be inserted through a small incision in the body of a patient and said proximal portion remaining externally of the body for manipulation by said surgeon, said distal portion of said second probe having a connector for detachably mounting said free edge of said membrane thereon whereby said membrane will be supported in its deployed position for retraction but can be returned to its stored position with respect to said distal portion of said first probe for removal from the body of the patient.

2. The retractor of claim 1, wherein said membrane, when assuming its stored position with respect to the distal portion of said first probe is substantially cylindrical.

3. The retractor of claim 1, wherein said membrane, when assuming its stored position with respect to the proximal portion of said first probe, is coiled with respect to said distal portion.

4. The retractor of claim 1, wherein said distal portion of said first probe rotates with respect to said proximal portion of said first probe to facilitate storage and deployment of said membrane.

5. The retractor of claim 1, wherein said distal portion of said second probe is detachably mounted on said free edge of said membrane by means of cooperating hooks and rings.

6. The retractor of claim 1, further comprising a third elongate probe having a distal portion and a proximal portion, said distal portion being adapted to be inserted through a small incision in the body of a patient and said proximal portion remaining externally of the body for manipulation by the surgeon, said distal portion engaging said membrane at a location intermediate said fixed and free edges of said membrane whereby said membrane is further supported during retraction.

7. A retractor for use in endoscopic surgery, comprising:
    first and second probes, each of said probes being independently manipulatable into a variety of positions, and each prove having a distal portion and a proximal portion, said distal portion being inserted through a small incision in the body of a patient and said proximal portion being manipulatable such that said distal portion may be positioned in the desired location; and
    a retractor surface mounted between and supported by said distal portions of said first and second probes for retracting tissues and organs and the like, said retractor surface being externally controlled by manual manipulation of said proximal portions of said probes.

8. The retractor of claim 7, wherein said retractor surface is elastic and flexible and is stretched between said distal portions of said first and second probes whereby damage to internal tissues and organs is avoided.

9. The retractor of claim 7, wherein the surface area of said retractor surface is adjustable.

10. The retractor of claim 7, further comprising a third probe engaging said retractor surface and position intermediate said first and second probes.

11. The retractor of claim 10, wherein said first probe has an extension whereby said first and third probes can be held in one hand such that a single surgeon can manipulate said retractor.

12. The retractor of claim 11, wherein said extension comprises at least one handle extending transversely away from said proximal portion of said first probe and in the direction of said third probe.

13. The retractor of claim 10, wherein each of said first, second, and third probes is provided with graduated marks to indicate the depth of insertion into the body of the patient.

14. The retractor of claim 7, further comprising a frame for holding said proximal portions of said first and second probes in place whereby manual manipulation is not necessary.

15. A retractor for use in endoscopic surgery comprising:
   a probe having proximal and distal portions, said distal portion being inserted through a first incision in the body of a patient and said proximal portion being manipulable to control the position of said distal portion;
   retraction means mounted in a coiled fashion on said distal portion of said probe whereby said retraction means is coiled for insertion through said first incision into the body of the patient and is uncoiled for retraction; and
   means for internally uncoiling said retraction means, said uncoiling means being independently manipulable from said probe and having proximal and distal portions, said distal portion being inserted through a second incision in the body of a patient and said proximal portion being manipulable to control the position of said distal portion for engaging and uncoiling said retraction means within the patient.

16. The retractor of claim 15, wherein said internal portion of said probe is rotatable with respect to said probe and said retraction means is coiled on said internal portion.

17. The retractor of claim 15, further comprising means on said proximal portion of said probe for controlling the rotation of said rotatable internal portion.

18. The retractor of claim 17, wherein said controlling means comprises a handle having an internal tip, said tip selectively engaging said rotatable internal portion of said probe in order to control the uncoiling of said retraction means.

19. A method of endoscopic retraction, comprising the steps of:
   a) inserting a distal end of a first probe through a first incision into the body of the patient, said first probe having a retraction device stored in the distal end thereof;
   b) inserting a distal end of a second probe, independent from said first probe, through a second incision, said second incision being different from said first incision;
   c) manually manipulating said second probe so that said distal end of said second probe engages the retraction device stored in the distal end of said first probe; and
   d) manually manipulating said first and second probes to cause said retraction device to be deployed into the desired retraction position.

20. The retraction method of claim 19, wherein said deployment step comprises the step of uncoiling said retraction device from the distal portion of said first probe.

21. The retraction method of claim 19, wherein said retraction device is uncoiled from the distal portion of said first probe by rotating said distal portion.

22. The retraction method of claim 19, further comprising the step of inserting a third probe through a third incision in the body of the patient and engaging the retraction device for further retractive support.

23. The retraction method of claim 19, further comprising the step of locking the retraction device in place once the desired retraction position has been assumed.

24. A retractor adapted for use in endoscopic surgery, comprising:
   a first elongate probe having a distal portion and a proximal portion, said distal portion being adapted to be removably inserted through a small incision in the body of a patient, said proximal portion remaining externally of the body for manipulation by a surgeon;
   a second elongate probe having a distal portion and a proximal portion, said distal portion being adapted to be inserted through a small incision in the body of a patient and said proximal portion remaining externally of the body for manipulation by the surgeon; and
   an elongate flexible membrane having two edges, at least one of said edges adapted to be removably attached to said distal portion of one of said elongate probes, and wherein said first probe and said second probe are joined only by attachment of said membrane to the distal portions of said probes, such that the membrane is externally controlled by manual manipulation of said proximal portions of said probes to provide retraction of tissue and organs and the like.

25. The retractor of claim 24, further comprising a third elongate probe having a distal portion and a proximal portion, said distal portion of said third probe engaging said flexible membrane to provide additional support during retraction.

26. The retractor of claim 25, wherein a loop is mounted on said flexible membrane midway along its length, such that said distal portion of said third probe engages said loop to provide additional support during retraction.

27. The retractor of claim 25, wherein each of said probes are hollow to facilitate the introduction of additional endoscopic surgical instruments into the patient's body.

28. A retractor adapted for use in endoscopic surgery, comprising:
   at least two elongate probes, each of said probes having a distal portion and a proximal portion, said distal portion being adapted to be removably inserted through a small incision in the body of a patient, said proximal portion remaining externally of the body for manipulation by a surgeon; and
   an elongate flexible membrane, wherein said elongate probes are joined only by attachment of said membrane with said distal portion of said probes, such that said membrane may be externally manipulated by said proximal portions of said probes to provide retraction of tissues and organs and the like in a variety of planar and non-planar positions.

29. The retractor of claim 28, wherein said membrane is coiled about the distal end of at least one of said probes during insertion into the patient's body.

30. A retractor adapted for use in endoscopic surgery on a body of a patient, comprising:
   a first elongate probe having a distal portion and a proximal portion, said distal portion being adapted to be removably inserted through a small incision in the body of the patient, said proximal portion remaining externally of the body for manipulation by a surgeon;

a second elongate probe having a distal portion and a proximal portion, said distal portion being adapted to be inserted through a small incision in the body of the patient, said proximal portion remaining externally of the body for manipulation by a surgeon, said second probe being independent of said first probe whereby said probes are independently manipulatable; and a retraction surface engaging the distal portion of said first probe for insertion into the body, said retraction surface adapted to be engaged by the distal portion of said second probe, said retraction surface being movable and positioned for retraction through the manipulation of said proximal portions of said probes, said retraction surface being capable of assuming a variety of positions with the body to provide retraction of tissues, organs and the like.

31. The retractor of claim 30, wherein said retraction surface comprises a flexible membrane so as to avoid damage to organs and tissues during retraction.

32. A retractor adapted for use in endoscopic surgery, comprising:

at least two independent probes, each of said probes having a distal portion and a proximal portion, said distal portion being adapted to be removably inserted through a small incision in the body of a patient, said proximal portion remaining externally of the body for manipulation; and a retraction surface, wherein said probes are joined only by engagement of said retraction surface with said distal portion of said probes, and wherein said retraction surface my be externally manipulated by said proximal portions of said probes to provide retraction of tissues and organs and the like in a variety of planar and non-planar positions.

33. A retractor for use in endoscopic surgery, comprising:

a first probe having proximal and distal portions, said distal portion being inserted into the body of a patient;

a retraction device mounted on said distal portion of said first probe; and a second probe having proximal and distal portions, said distal portion being engageable with said retraction device mounted on said distal portion of said first probe, said proximal portion of said second probe being externally manipulable to at least partially deploy said retraction device, whereby retraction of tissues, organs and the like may occur.

34. A method for providing retraction during endoscopic surgery, comprising the steps of:

(a) inserting into the body of a patient a first probe having a proximal end and a distal end, said proximal end of said first probe remaining outside the body for manipulation;

(b) causing said distal end of said first probe to engage a retraction surface;

(c) inserting into the body of the patient a second probe having a proximal end and a distal end, said proximal end of said second probe remaining outside the body for manipulation;

(d) causing said distal end of said second probe to engage said retraction surface; and (e) manipulating said first and second probes such that said retraction surface retracts desired tissue inside the patient's body.

* * * * *